(12) United States Patent
Wang et al.

(10) Patent No.: US 10,987,185 B2
(45) Date of Patent: Apr. 27, 2021

(54) STERILITY BREACH DETECTION SYSTEM AND CONTROLLER SYSTEM FOR A STERILIZATION CONTAINER

(71) Applicant: O&M Halyard, Inc., Mechanicsville, VA (US)

(72) Inventors: Ruoya Wang, Decatur, GA (US); Anne E. Cote, Milton, GA (US); Kun-Chi Wu, Johns Creek, GA (US); Tracy J. White, Cumming, GA (US); Vernon Meadows, Lilburn, GA (US); Edward B. Madsen, Cumming, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 194 days.

(21) Appl. No.: 16/145,497

(22) Filed: Sep. 28, 2018

(65) Prior Publication Data

US 2020/0100858 A1 Apr. 2, 2020

(51) Int. Cl.
| | |
|---|---|
| *A61B 50/30* | (2016.01) |
| *A61B 90/40* | (2016.01) |
| *A61L 2/28* | (2006.01) |
| *A61L 2/07* | (2006.01) |
| *A61B 90/00* | (2016.01) |

(52) U.S. Cl.
CPC .............. *A61B 50/30* (2016.02); *A61B 90/40* (2016.02); *A61B 2090/081* (2016.02); *A61L 2/07* (2013.01); *A61L 2/28* (2013.01); *A61L 2202/182* (2013.01)

(58) Field of Classification Search
CPC ............ A61B 50/30; A61B 90/40; A61L 2/28
See application file for complete search history.

(56) References Cited

U.S. PATENT DOCUMENTS

| | | | |
|---|---|---|---|
| 5,351,324 A | 9/1994 | Forman | |
| 5,443,801 A * | 8/1995 | Langford | ........... A61B 1/00059 422/294 |
| 5,565,634 A | 10/1996 | Graessle et al. | |
| 5,581,019 A * | 12/1996 | Minor | ....................... G01L 1/20 73/114.77 |

(Continued)

FOREIGN PATENT DOCUMENTS

| | | |
|---|---|---|
| AU | 756194 | 1/2003 |
| CN | 107355464 A | 11/2017 |

(Continued)

*Primary Examiner* — Kevin Joyner
(74) *Attorney, Agent, or Firm* — Dority & Manning, P.A.

(57) ABSTRACT

The present disclosure provides sterilization containers with features for sealing a volume against an ingress of contaminants. The present disclosure also provides a sterility breach detection system for detecting whether the sterilization container seal has been breached, which potentially could compromise the sterility of any contents of the container. Further, the present disclosure provides a controller system for detecting, tracking, and alerting a user to the state of a sterilization container, such as whether the container seal has been breached. The sterility breach detection system and/or the controller system may utilize a smart gasket to detect breaches in a seal of a sterilization container, and a controller in operative communication with the smart gasket may activate an indicator to alert a user to a detected breach in the seal.

20 Claims, 12 Drawing Sheets

(56) References Cited

U.S. PATENT DOCUMENTS

| | | | |
|---|---|---|---|
| 6,002,501 | A | 12/1999 | Smith et al. |
| 6,003,872 | A | 12/1999 | Nord |
| 6,295,330 | B1 | 9/2001 | Skog et al. |
| 6,590,409 | B1 | 7/2003 | Hsiung et al. |
| 7,018,592 | B2 | 3/2006 | Bowen |
| 8,470,601 | B2 | 6/2013 | Foley et al. |
| 9,393,077 | B2 | 7/2016 | Schuster |
| 2003/0095891 | A1 | 5/2003 | O'Neal |
| 2006/0243625 | A1 | 11/2006 | Biddick et al. |
| 2007/0094303 | A1 | 4/2007 | Zwingenberger et al. |
| 2010/0247388 | A1* | 9/2010 | Buczynski ............... A61L 2/07 422/112 |
| 2012/0152957 | A1 | 6/2012 | Smith |
| 2013/0280134 | A1 | 10/2013 | Hoffman et al. |
| 2014/0320268 | A1 | 10/2014 | Burke |
| 2015/0165081 | A1 | 6/2015 | Kozin |
| 2015/0374868 | A1 | 12/2015 | Bruce et al. |
| 2016/0095310 | A1 | 4/2016 | Anderson et al. |
| 2016/0250361 | A1 | 9/2016 | Lukas |
| 2017/0224859 | A1 | 8/2017 | Broninx et al. |

FOREIGN PATENT DOCUMENTS

| | | |
|---|---|---|
| CN | 105605078 B | 7/2018 |
| EP | 1 230 936 A1 | 8/2002 |
| GB | 2 295 018 A | 5/1996 |
| WO | WO 95/06237 A1 | 3/1995 |
| WO | WO 2014/120074 A2 | 8/2014 |
| WO | WO 2015/076746 A1 | 5/2015 |
| WO | WO 2016/156828 A1 | 10/2016 |
| WO | WO 2017/024260 A1 | 2/2017 |
| WO | WO 2017/044906 A2 | 3/2017 |

\* cited by examiner

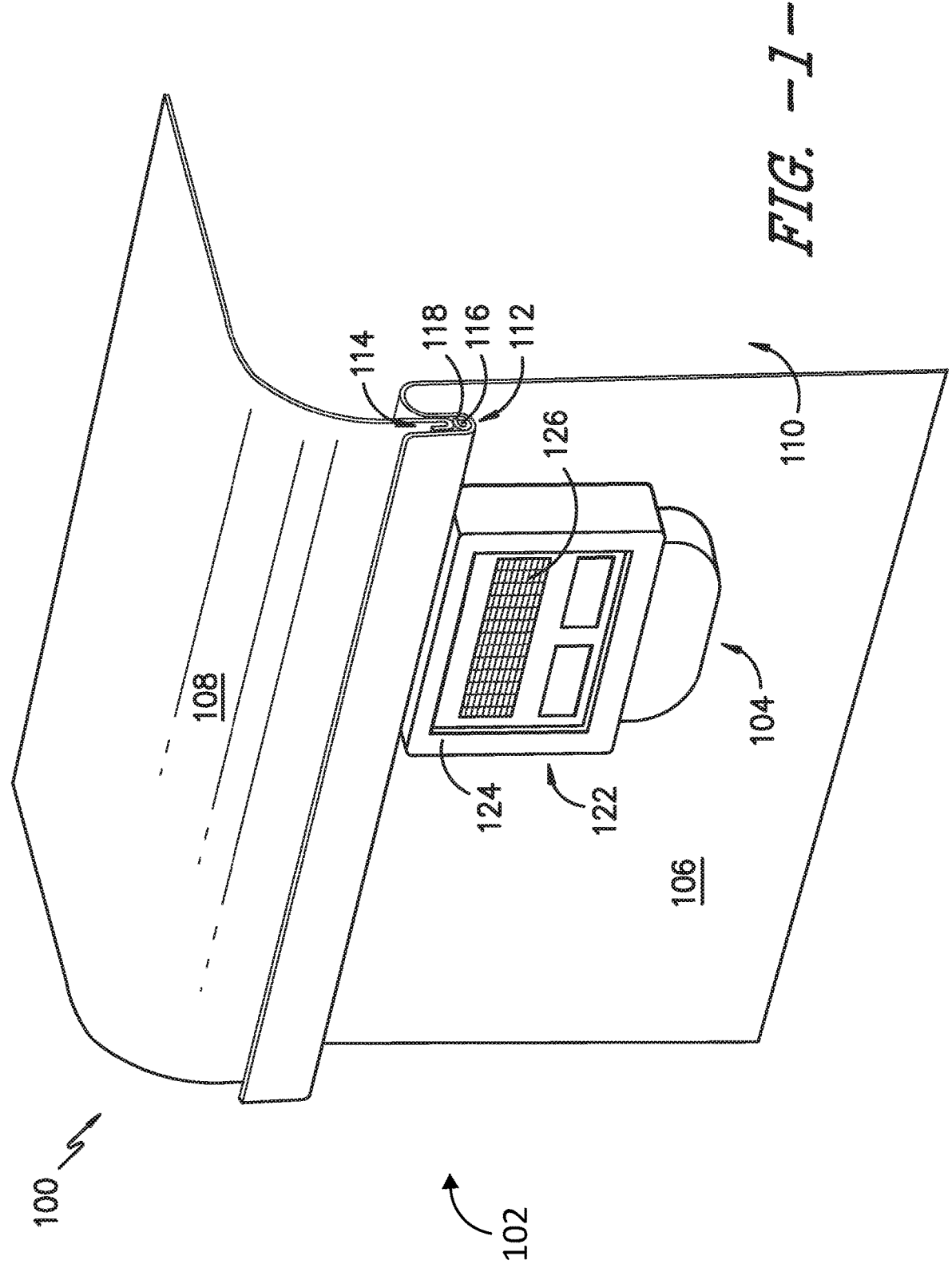
FIG. -1-

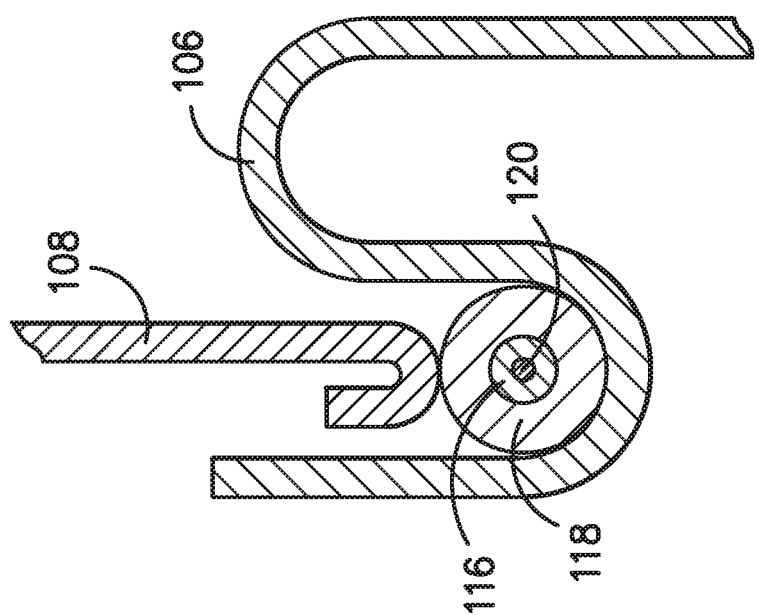
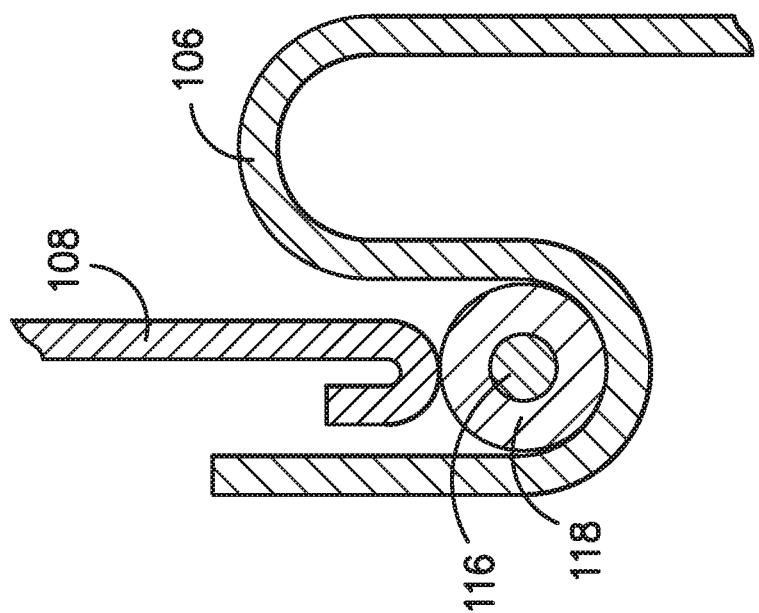

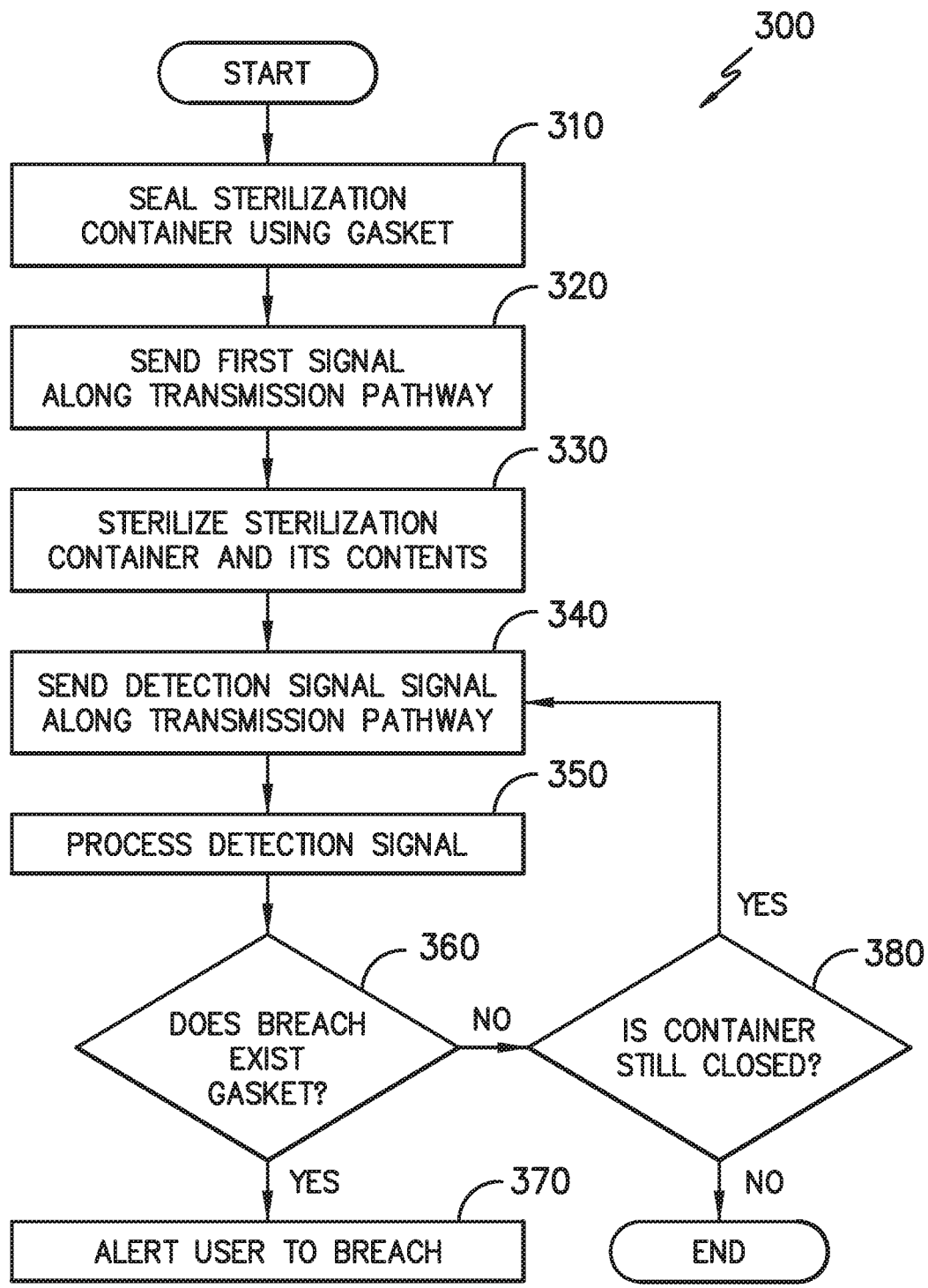
FIG. -3-

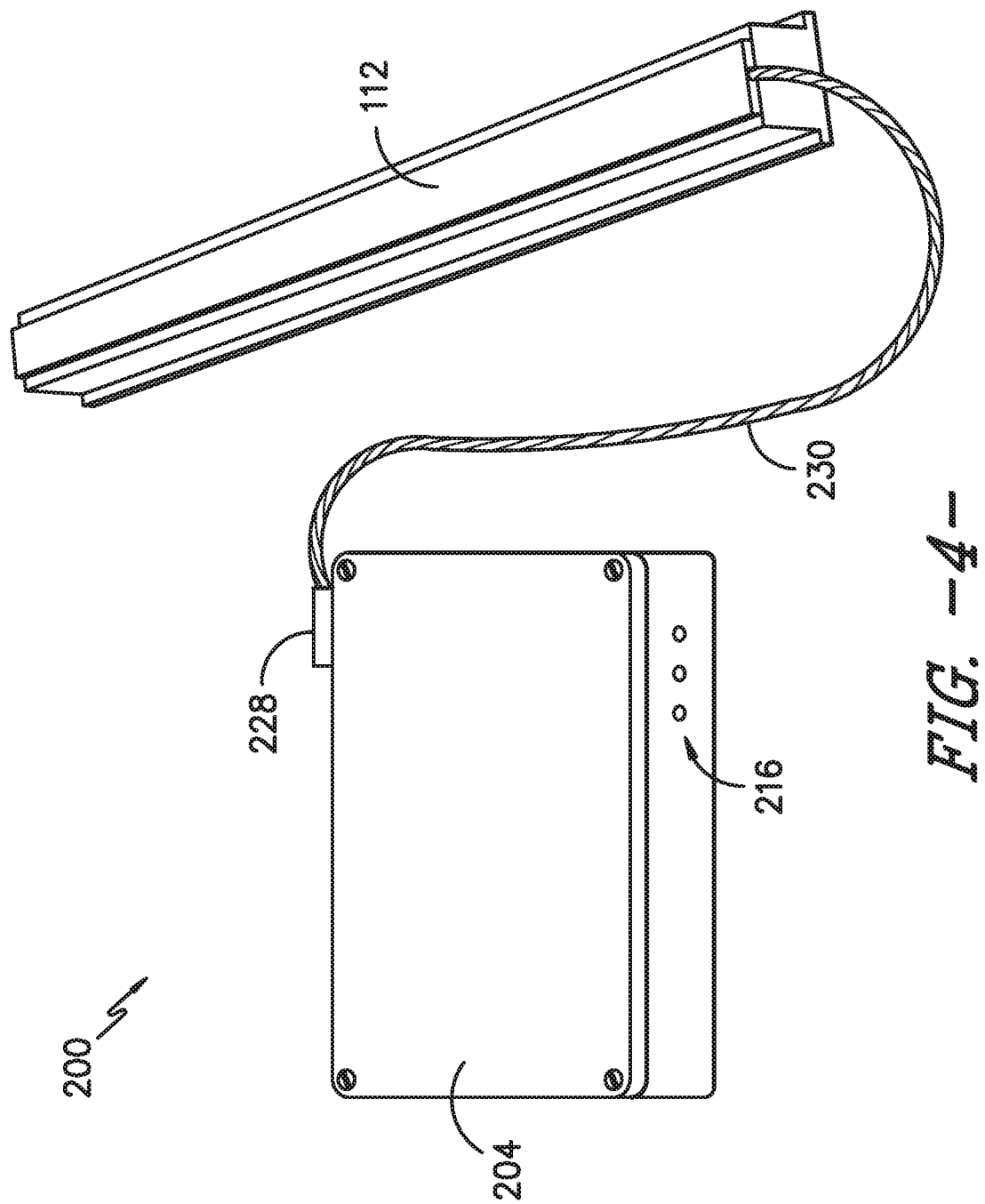
FIG. -4-

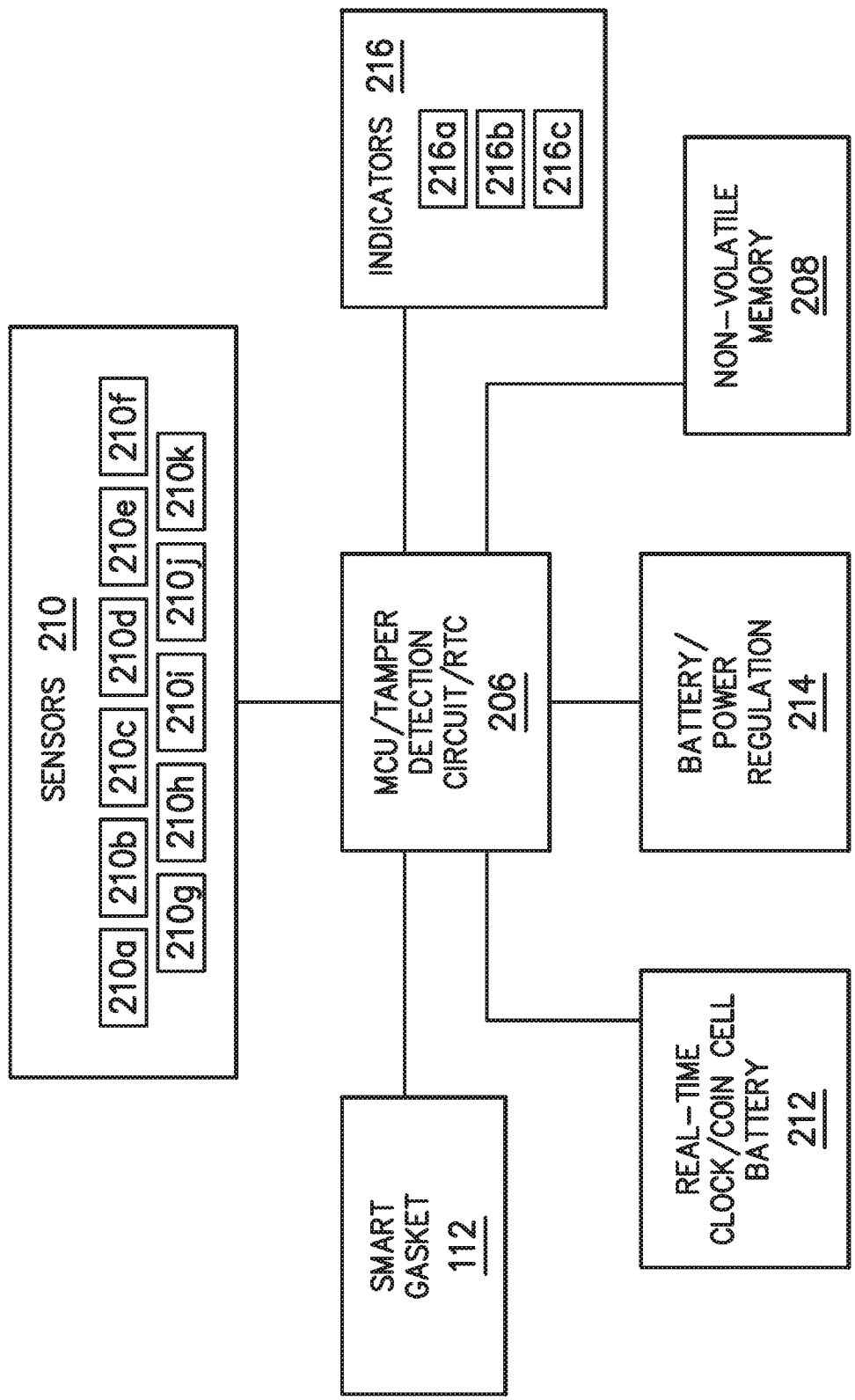
FIG. -5-

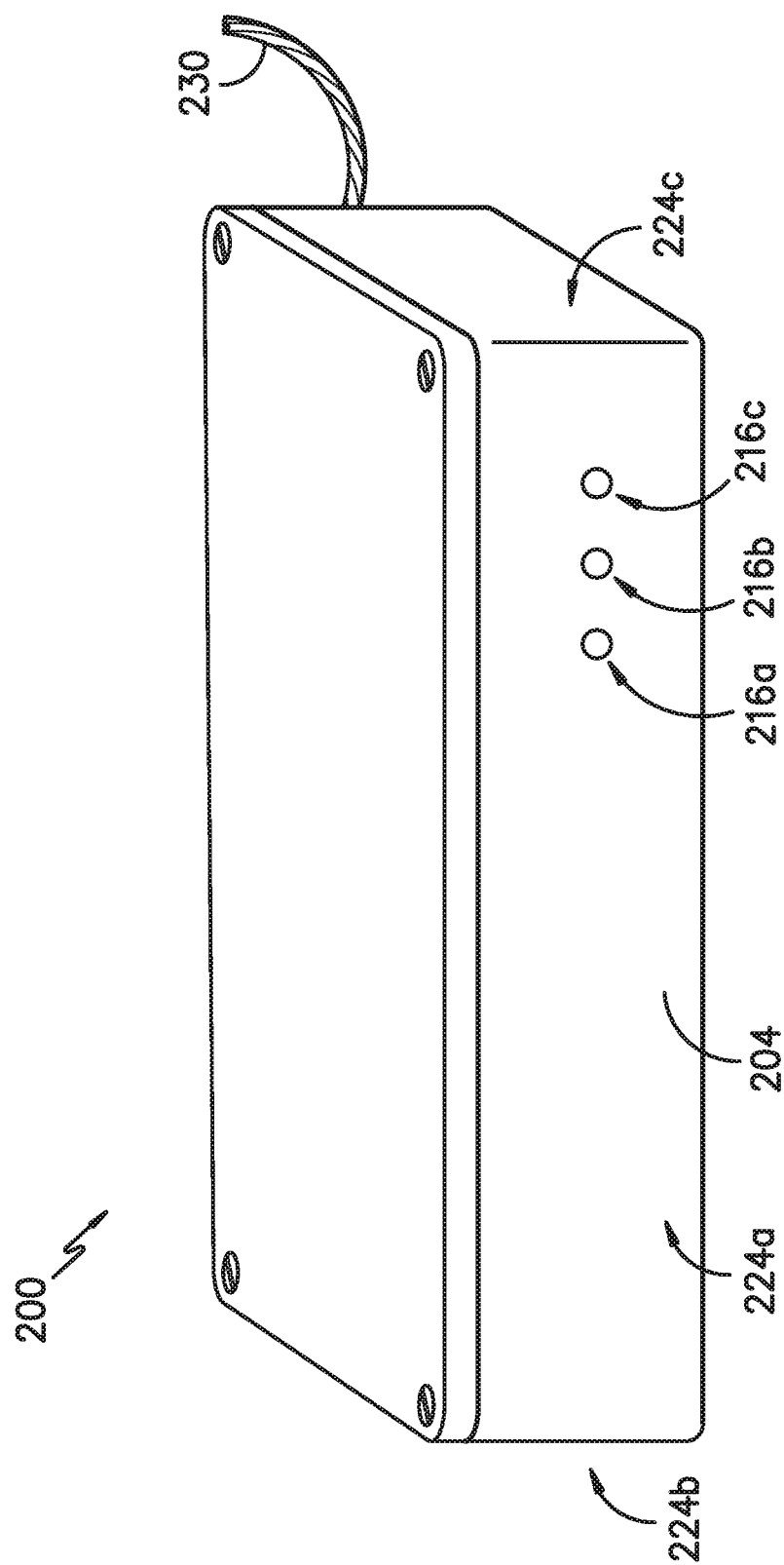
FIG. -6-

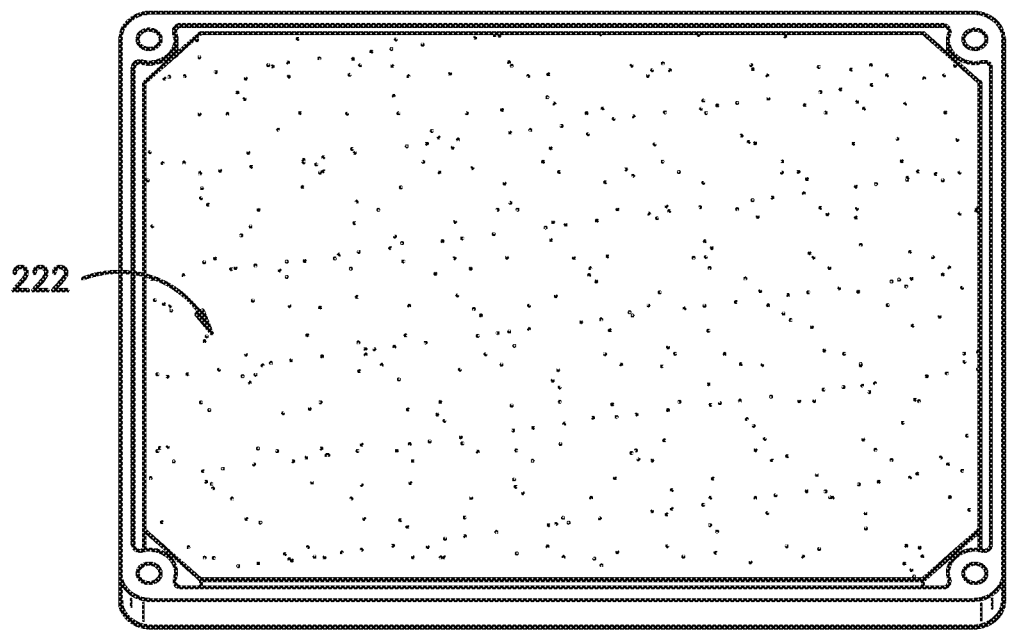
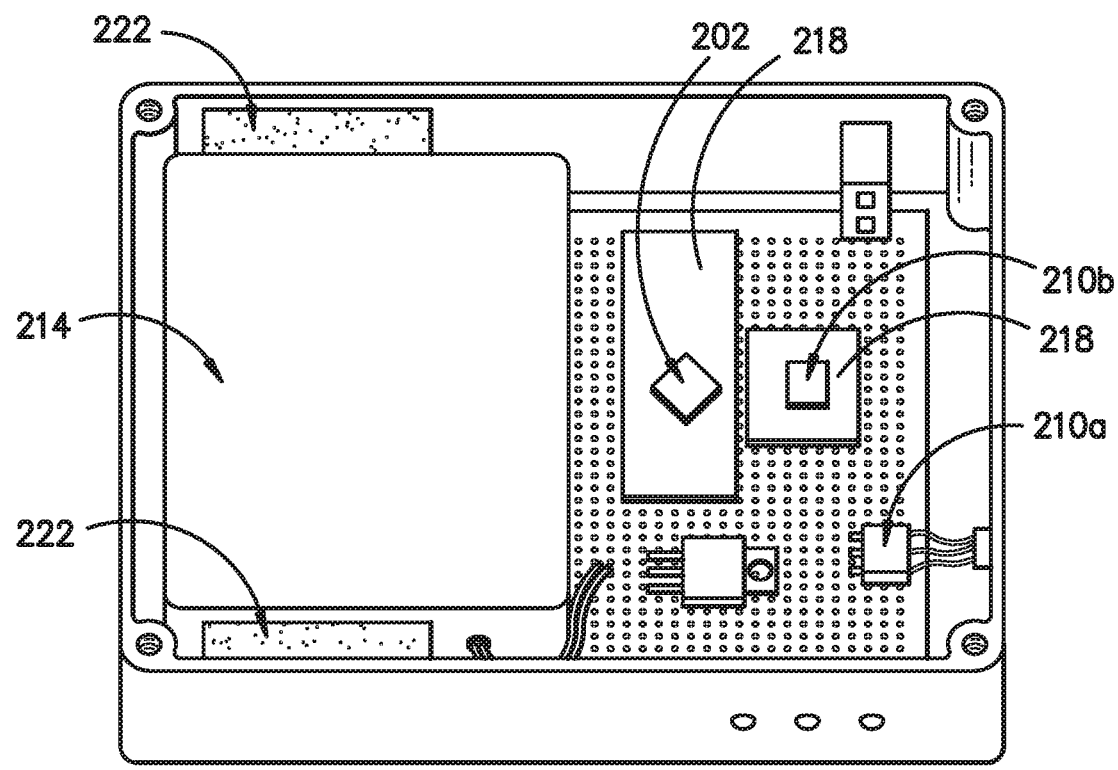
FIG. —7—

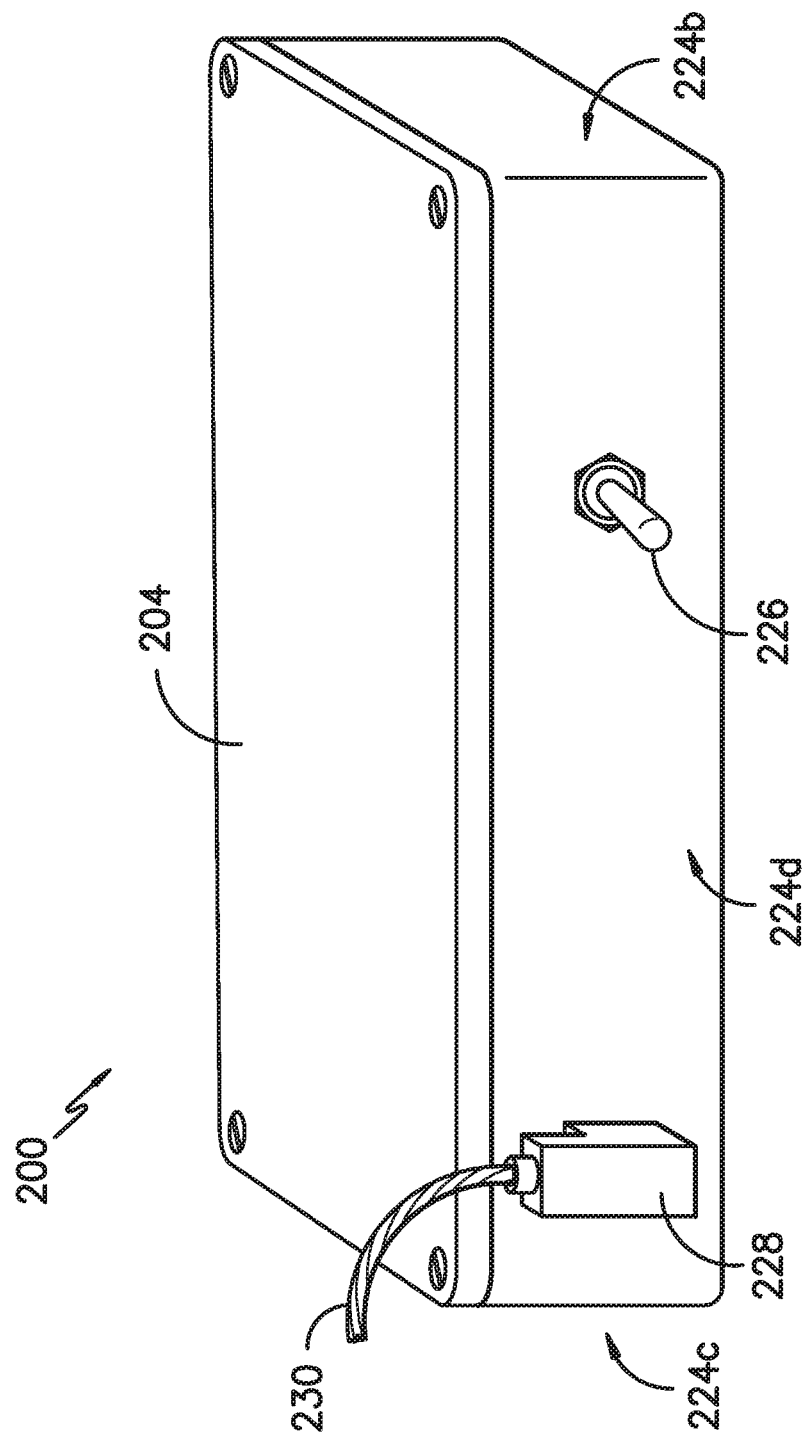
FIG. -8-

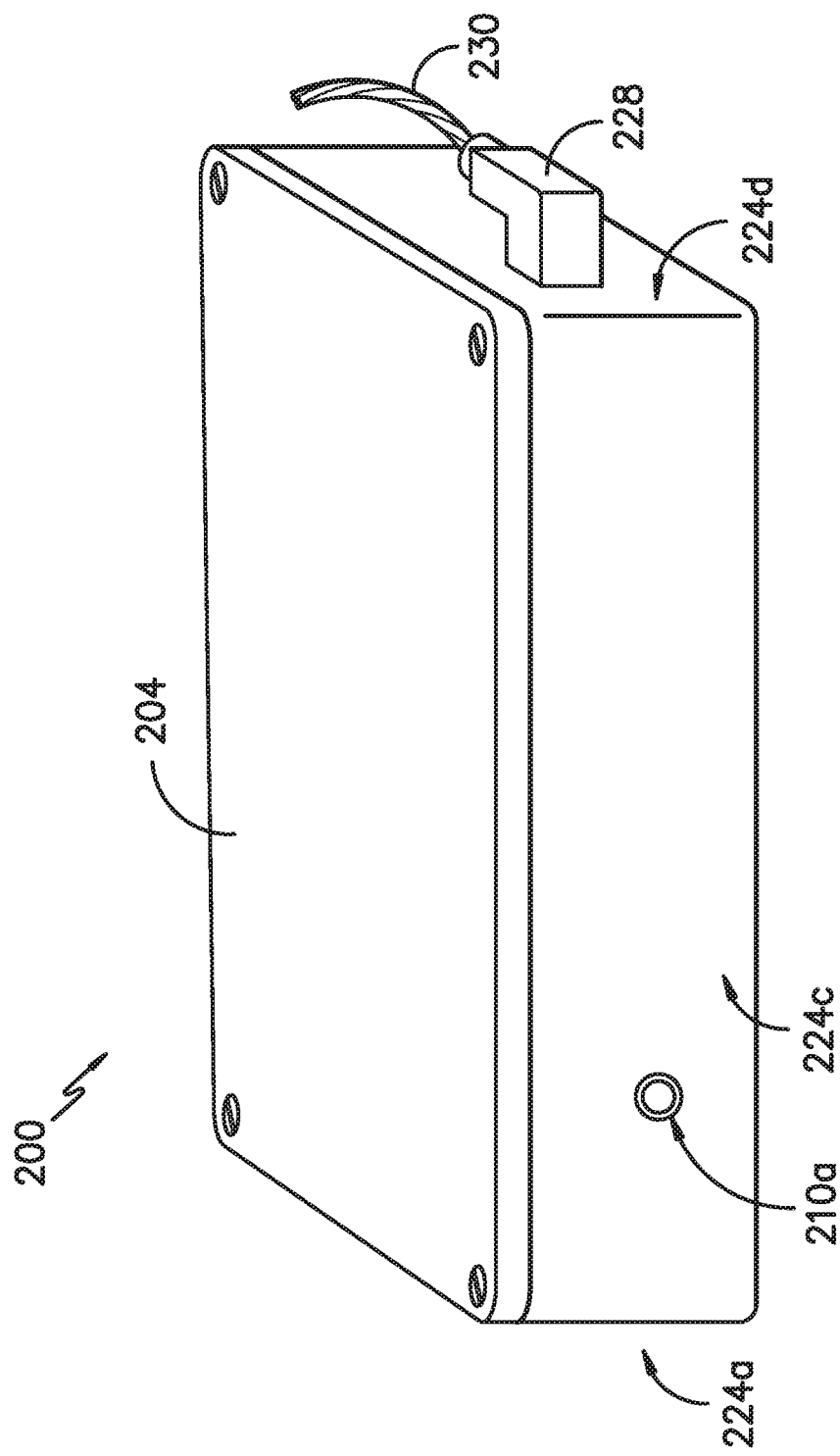

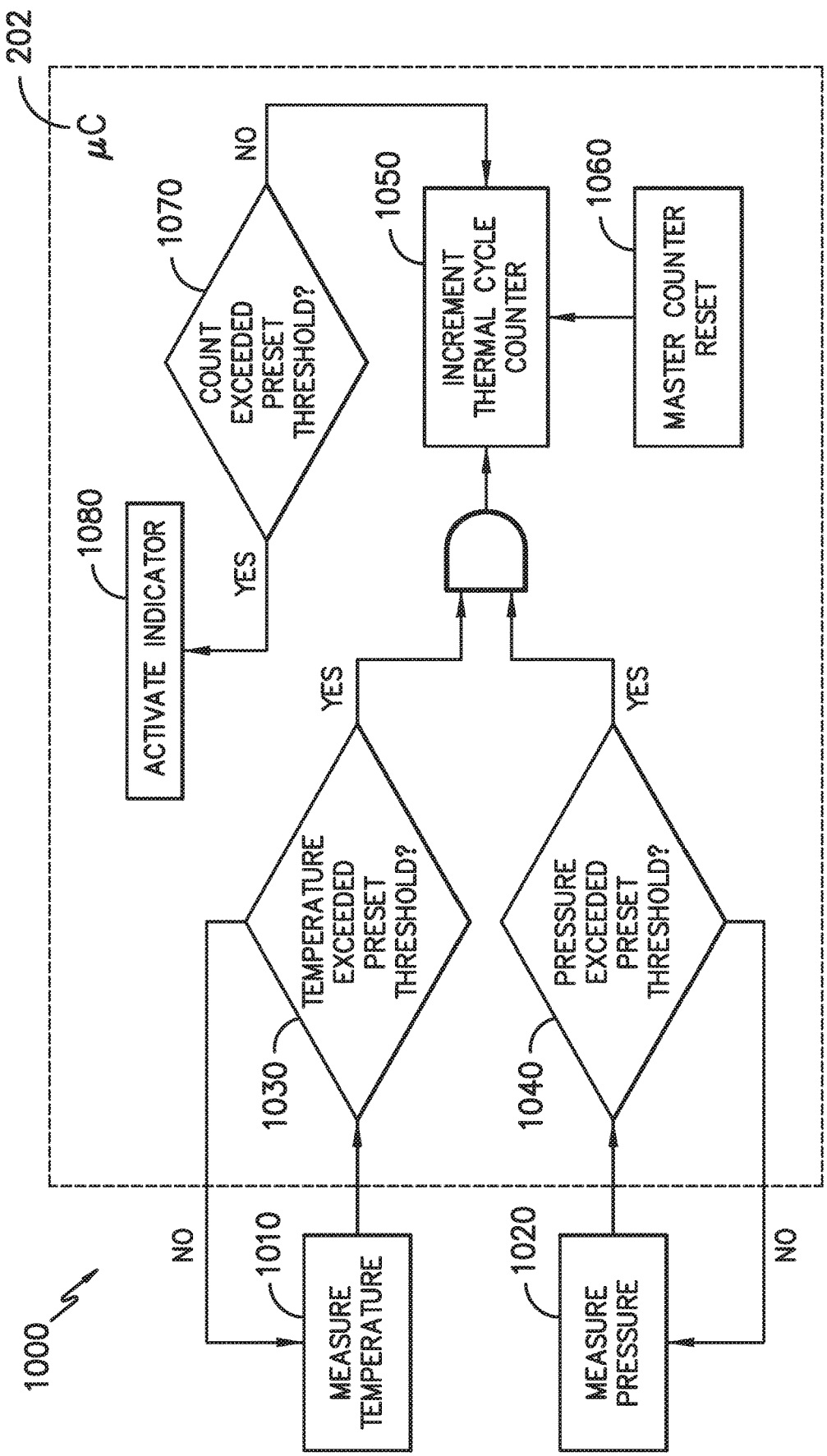
FIG. -10-

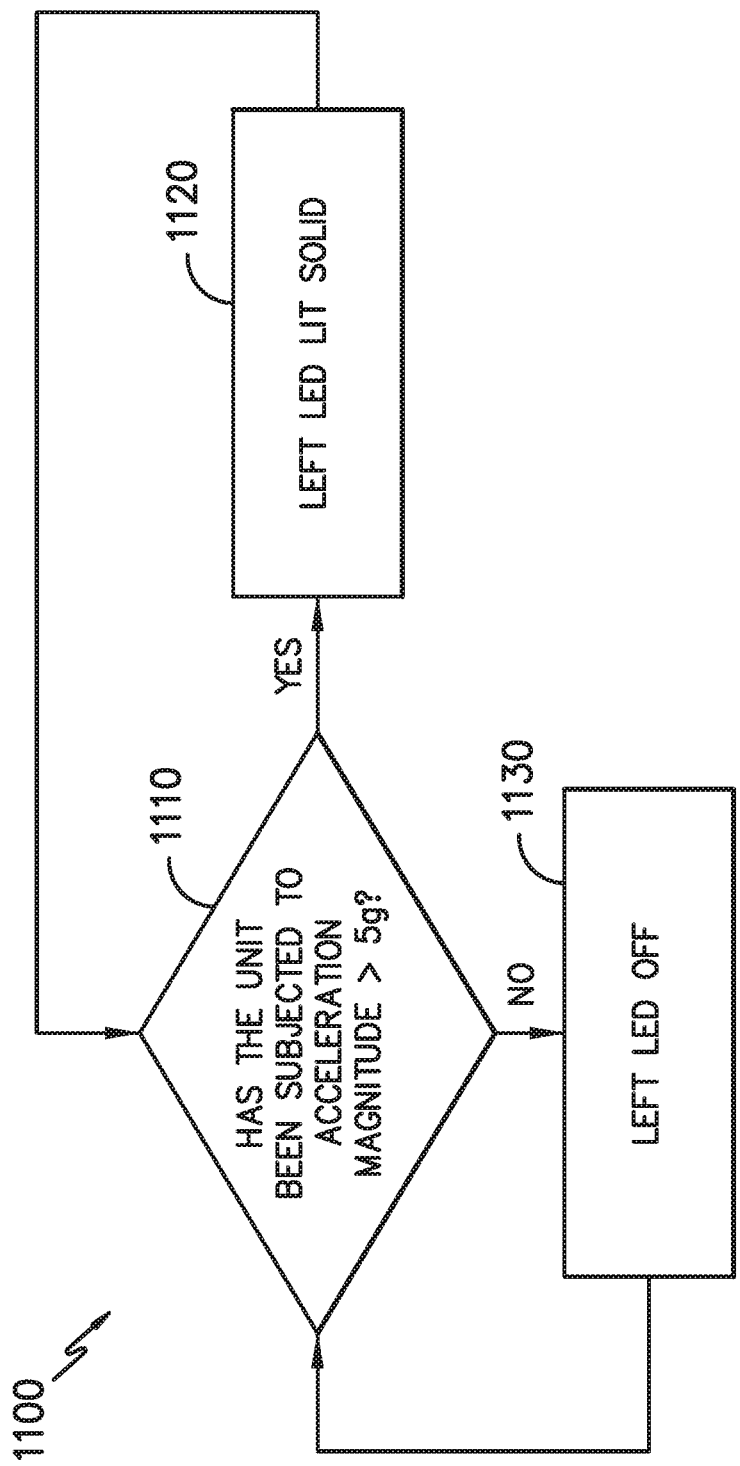
FIG. -11-

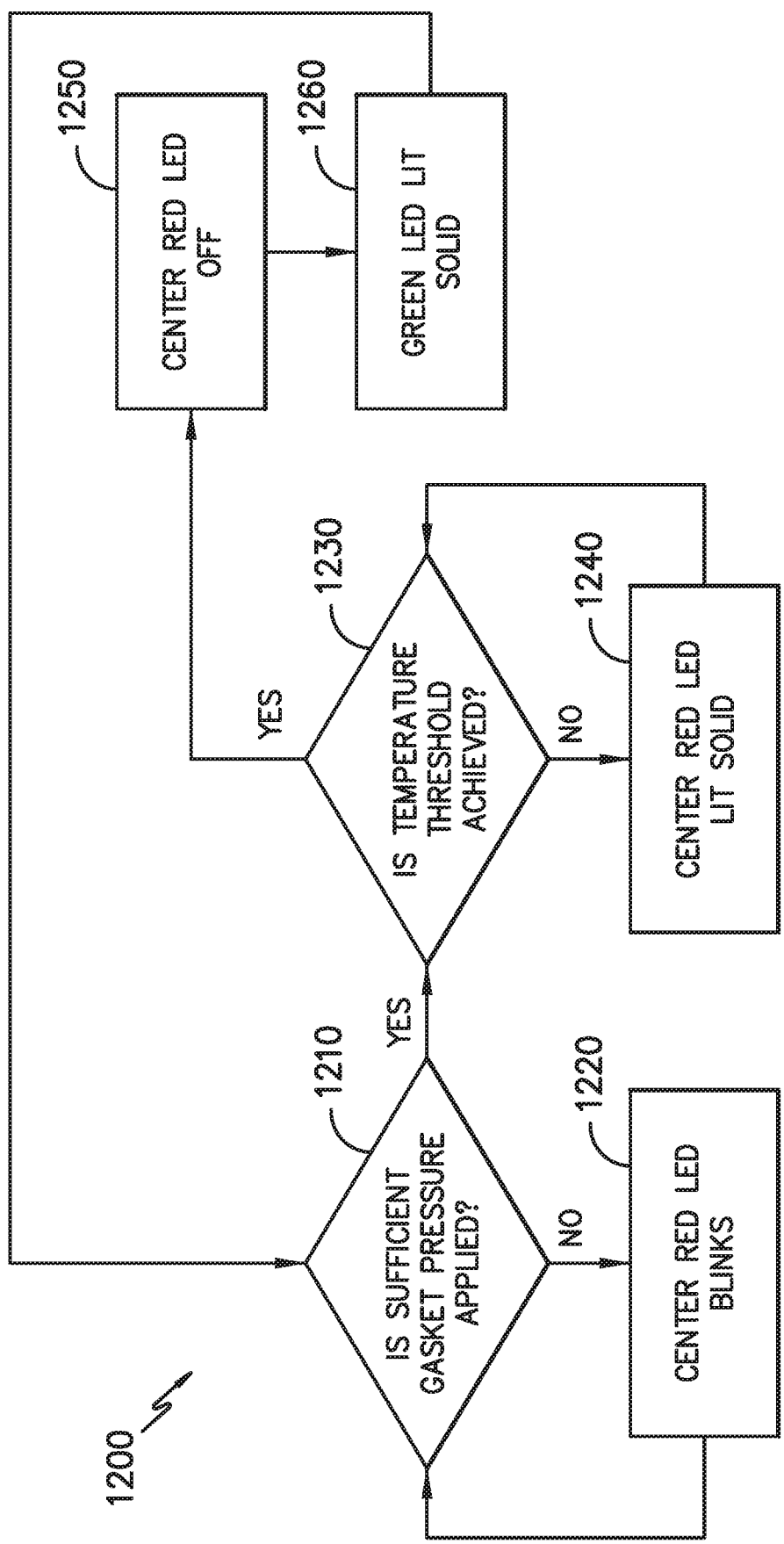
FIG. -12-

STERILITY BREACH DETECTION SYSTEM AND CONTROLLER SYSTEM FOR A STERILIZATION CONTAINER

FIELD

The subject matter of the present disclosure relates generally to sterilization containers and, more particularly, to sterility breach detection systems and controller systems for sterilization containers.

BACKGROUND

Many of the surgical instruments and supplies used in an operating room (OR) are reusable. These supplies typically include such things as clamps, scalpel blade handles, retractors, forceps, scissors, surgeon's towels, basins, and the like. All of these supplies must be collected after each procedure, decontaminated, placed in a sterilization container, and sterilized before they can be used again in another procedure. The sterilization container or packaging system used must be of the size and shape to accommodate the items to be sterilized and must be compatible with and withstand the physical conditions of the sterilization process. Typical sterilization containers include disposable wraps and reusable rigid container (RCs), which include a lid, a body, a filter, and one or more sealing gaskets. Typical means of sterilizing instruments include, among others, autoclaving with steam, exposure to ethylene oxide gas, and exposure to hydrogen peroxide plasma, as is done with the STERRAD® Sterilization System from Advanced Sterilization Products, Irvine, Calif. After the package and its contents have been sterilized, the sterilization package typically is stored until it is needed for a surgical procedure.

Preventing postoperative infection is critically important in surgical procedures. The use of properly sterilized surgical instruments is a key piece of the infection prevention paradigm. Sterilization container systems are designed to allow for proper steam penetration, post-autoclave cooling, indefinite aseptic storage of the instruments, and aseptic opening and removal of the instruments. RCs exhibit good durability and due to their reusability, represent a very economical sterilization method. However, quickly assessing that the container has undergone adequate thermal cycling for sterilization as well as determining whether any container breach has occurred post-autoclave, such as during storage, is difficult and remains a challenge. Breaches to an RC's internal aseptic environment can occur during post-autoclave storage or transport to the OR due to several reasons, including weakening or aging of sealing gaskets, damage to the sealing surface of the lid, body, and/or filter, and/or accidental opening and closing of the lid. These breaches are generally very difficult if not impossible to detect and can represent a serious source of pathogen ingress. Continuous monitoring of the seal interface quality and detection and indication of any breach during the sterilization chain is critically important to ensure the instruments remain sterile prior to use. Current RC systems generally have crude heat-activated colorimetric or bimetal indicators that show the RC has been subjected to a thermal cycling and that the lid has not been opened. Other than these simple indicators, however, current RC systems are not able to detect breaches to the sealing interface, especially breaches that are difficult to be visually noticed, or to quickly indicate whether the contents of the RC system is sterile.

Consequently, there is a need for a sterilization container that overcomes the shortcomings of known sterilization containers. In particular, a sterility breach detection system having features for detecting and alerting a user to a breach in a sterilization container seal would be beneficial. Further, such a detection system, which may be a gasket referred to as a smart gasket, that utilizes a signal to detect and alert the user to the breach would be useful. Additionally, a controller system for detecting, tracking, and alerting a user to the state of a sterilization container would be advantageous. Such a controller system that works with a sterility breach detection system to detect and alert the user to breaches in the container's sterility would be desirable.

SUMMARY

The present disclosure provides sterilization containers with features for sealing a volume against an ingress of contaminants. The present disclosure also provides a sterility breach detection system for detecting whether the sterilization container seal has been breached, which potentially could compromise the sterility of any contents of the container. Further, the present disclosure provides a controller system for detecting, tracking, and alerting a user to the state of a sterilization container, such as whether the container seal has been breached. Additional aspects and advantages of the invention will be set forth in part in the following description, may be apparent from the description, or may be learned through practice of the invention.

In one aspect, the present subject matter is directed to a sterilization container system. The sterilization container system comprises a sterilization container including a container body and a container lid that together define a container interior. The sterilization container also includes a container gasket for sealing the container interior against an ingress of contaminants and a transmission pathway embedded in the container gasket. The sterilization container system further comprises a controller. The controller is configured to process a signal transmitted along the transmission pathway to determine whether a breach exists in the container gasket. It should be understood that the sterilization container system may be further configured with any suitable additional features as described herein.

In another aspect, the present subject matter is directed to a sterility breach detection system for a sterilization container. The sterilization container includes a body and a lid that together define an interior. The sterility breach detection system comprises a seal for sealing the interior against an ingress of contaminants, a transmission pathway, and a controller. The controller is configured to process a signal transmitted along the transmission pathway to determine whether a breach exists in the seal. It should be appreciated that the sterility breach detection system may be further configured with any suitable additional features as described herein.

In still another aspect, the present subject matter is directed to a method for detecting a breach in sterility of a sterilization container. The method comprises sealing the sterilization container using a gasket that extends between a container body and a container lid, sending a detection signal along a transmission pathway embedded in the gasket, processing the detection signal, and determining whether a breach exists in the gasket. It should be understood that the method may be further configured with any suitable additional features as described herein.

In yet another aspect, the present subject matter is directed to a sterilization container system. The sterilization container system comprises a sterilization container including a container body and a container lid that together define a container interior, a sensor attached to the sterilization container, an indicator for indicating a state of the sterilization container to a user of the sterilization container, and a controller in operative communication with the sensor. The controller is configured to process data from the sensor to activate the indicator. It should be appreciated that the sterilization container system may be further configured with any suitable additional features as described herein.

In a further aspect, the present subject matter is directed to a sterilization container system. The sterilization container system comprises a sterilization container including a container body and a container lid that together define a container interior, at least two sensors attached to the sterilization container, and a controller in operative communication with the at least two sensors. The controller is configured to process data from the at least two sensors to indicate a state of the sterilization container to a user of the sterilization container. It should be understood that the sterilization container system may be further configured with any suitable additional features as described herein.

In yet a further aspect, the present subject matter is directed to a sterilization container system that comprises a sterilization container including a container body and a container lid that together define a container interior, a container gasket for sealing the container interior against an ingress of contaminants, and a transmission pathway embedded in the container gasket. The sterilization container system also comprises a plurality of sensors, an indicator for indicating a state of the sterilization container to a user of the sterilization container, and a controller in operative communication with the transmission pathway and the plurality of sensors. The controller is configured to process a signal transmitted along the transmission pathway to determine whether a breach exists in the container gasket. The controller also is configured to activate the indicator to indicate to a user that a breach exists in the container gasket.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a perspective view of a portion of a sterilization container assembly having a sterilization container and a sterility breach detection system, according to an exemplary embodiment of the present subject matter.

FIG. 2A provides a cross-section view of the sterilization container and a gasket of the sterilization container assembly of FIG. 1, according to an exemplary embodiment of the present subject matter.

FIG. 2B provides a cross-section view of the sterilization container and a gasket of the sterilization container assembly of FIG. 1, according to another exemplary embodiment of the present subject matter.

FIG. 3 provides a flow diagram illustrating a method for detecting a breach in sterility of the sterilization container of the sterilization container assembly of FIG. 1.

FIG. 4 provides a top, perspective view of a controller system and smart gasket, according to an exemplary embodiment of the present subject matter.

FIG. 5 provides a block diagram of the controller system of FIG. 4.

FIG. 6 provides a side view of a first side of the controller system of FIG. 4.

FIG. 7 provides an interior view of the controller system of FIG. 4.

FIG. 8 provides a side view of a second side of the controller system of FIG. 4.

FIG. 9 provides a side view a third side of the controller system of FIG. 4.

FIG. 10 provides a flow diagram illustrating a logic sequence of the controller system of FIG. 4.

FIG. 11 provides a flow diagram illustrating another logic sequence of the controller system of FIG. 4.

FIG. 12 provides a flow diagram illustrating yet another logic sequence of the controller system of FIG. 4.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Described herein are a sterilization packaging system or container and components thereof suitable for use in a variety of procedures for containing, sterilizing, storing, and using sterilized items such as surgical devices, instruments, or supplies. While described in conjunction with its use in surgical room procedures located in hospitals or ambulatory surgical facilities, the present subject matter is intended for use wherever there is a need for containerized sterilized devices, instruments, or materials. Consequently, the following description should not be considered a limitation as to the scope of use of the present subject matter.

Referring particularly to FIG. 1, a perspective cross-section view is provided of a portion of a sterilization container assembly 100, according to an exemplary embodiment of the present subject matter. As shown in FIG. 1, the sterilization container assembly 100 comprises a reusable rigid sterilization container 102 and a controller 104. The sterilization container 102 includes a container body 106 and a container lid 108. The container body 106 and container lid 108 together define a container interior 110. The sterilization container 102 is by way of example only; other containers 102 having different configurations may be used as well.

The sterilization container 102 further includes a container gasket 112, which forms a seal for sealing the container interior 110 against an ingress of contaminants. That is, when properly compressed between the container body 106 and lid 108, the container gasket 112 prevents contaminants from entering the container interior 110, such that the container contents, e.g., surgical instruments, tools, or the like disposed within the sterilization container 102, remain sterile after the container 102 and its contents are subjected to a sterilization protocol. The container gasket 112 defines a sealing pathway that extends about the perimeter of the container body 106 and the perimeter of the container lid 108, i.e., the sealing pathway extends between the body 106 and lid 108 about the entire perimeter of the sterilization container 102 to provide a seal between the body 106 and lid 108.

In some embodiments, the container gasket 112 is provided in the container body 106, e.g., in a recess into which a portion of the container lid 108 is received as shown in FIGS. 1, 2A, and 2B. In other embodiments, the container gasket 112 is provided in the container lid 108, e.g., in a recess into which a portion of the container body 106 is received. In still other embodiments, the container gasket 112 is separate from the container body 106 and lid 108 and is positioned between the body 106 and lid 108 as part of an assembly process for closing and sealing the container interior 110, e.g., the container gasket 112 may be positioned along a rim of the body 106 before the lid 108 is secured to the body 106.

Turning to FIGS. 2A and 2B, in exemplary embodiments of the sterilization container assembly 100, the container gasket 112 is a "smart" gasket. Generally, a smart gasket is a gasket with electronically relevant components, i.e., the gasket fulfills a primary purpose of providing a seal between two surfaces but within which is embedded passive and/or active electronic components. More particularly, using a technology such as time domain reflectometry (TDR), the smart gasket 112 may be part of a sterility breach detection system 114 for assessing the quality of the seal between the container body 106 and container lid 108. The sterility breach detection system 114 includes the controller 104 and a transmission pathway 116 embedded in the gasket 112. The controller 104 is configured to process a signal transmitted along the transmission pathway 116 to determine whether a breach exists in the seal, i.e., the container gasket 112.

A TDR transmission pathway in the gasket 112, such as transmission pathway 116, may comprise a plurality of wires that are electronic waveguides used to interrogate physical non-uniformities in the gasket 112 based on changes in local compression of the gasket 112, which changes the dielectric strength between the wires. TDR involves four main components, namely a signal injector, a transmission pathway, a signal detector, and a signal processor. The signal injector launches an electrical signal consisting of a very sharp rising edge into the transmission pathway, as this electrical signal propagates down the transmission pathway, any changes to the impedance of the pathway attenuates or characteristically changes the signal. As the signal reaches the end of the pathway and is reflected to the source, a detector, also located at the source end, detects the reflected shape of the signal. By comparing the shape and size (e.g., the area under the curve) of the reflected signal to the source signal, information can be gained on the state of the transmission pathway. Thus, where the sterility breach detection system 114 utilizes TDR to detect a breach in the seal, the controller 104 may be the signal injector, detector, and processor, and the transmission pathway 116 is the transmission pathway for the signal. Accordingly, the controller 104 may send a detection signal along the transmission pathway 116, detect a reflected signal, and process the reflected signal to determine whether the container gasket 112 has been breached. It will be appreciated that the transmission pathway 116 is coextensive with the sealing pathway defined by the gasket 112 such that the transmission pathway 116 can detect breaches along the entire sealing pathway.

In exemplary embodiments of the sterilization container assembly 100 and sterility breach detection system 114, the transmission pathway 116 comprises one or more metal wires and each of the container body 106 and container lid 108 are formed from a metallic material such that the container body 106 is metallic and the container lid 108 is metallic. As shown in the figures, the transmission pathway 116 extends through a gasket material 118. Where the transmission pathway 116, container body 106, and container lid 108 are each formed from a metallic material, the gasket material 118 is a dielectric material disposed between the metal wire transmission pathway 116, the metallic container body 106, and the metallic container lid 108.

As further depicted in the figures, the smart gasket 112 may have different configurations. For example, as shown in FIG. 2A, the transmission pathway 116 extends within a gasket material 118 and at least one grounded point, e.g., the transmission pathway 116 is grounded at one end of the pathway 116. The configuration shown in FIG. 2A may be referred to as a reference ground approach. As another example, illustrated in FIG. 2B, the transmission pathway 116 extends with the gasket material 118, and a ground wire 120 extends through the transmission pathway 116 such that the ground wire 120 is coaxial with the pathway 116. The configuration shown in FIG. 2B may be referred to as a coaxial approach. The transmission pathway 116 may be grounded in other ways as well, and the smart gasket 112 and sterility breach detection system 114 also may have other configurations than as illustrated.

It will be appreciated that the dielectric gasket material 118 generally is compressible and may be compressed between the container body 106 and the container lid 108 to seal the body 106 to the lid 108. As the gasket 112 is compressed between the body 106 and lid 108, the local dielectric properties of the gasket 112 change, which changes the local impedance of the transmission pathway 116 such that the pathway 116 includes local variances in impedance. To assess the quality of the seal provided by the container gasket 112, a baseline measurement is first taken and stored of the compressed gasket 112 during assembly or immediately following the replacement of an old gasket with a new one. Over time, the container gasket 112 degrades and loses elasticity or the sealing surface may become damaged, which results in poor gasket compression. Accordingly, the signal of the degraded or damaged gasket 112 is characteristically different compared to the baseline signal measurement. Thus, as described in greater detail herein, the sterility breach detection system 114 may compare signals transmitted along the transmission pathway 116 to the baseline signal measurement to determine if the seal provided by the gasket 112 has been breached. In some embodiments, when the signal of the degraded or damaged gasket 112 exceeds a preset threshold, the controller 104 may activate a gasket replacement indicator 122 to alert a user to replace the gasket 112.

Referring back to FIG. 1, the controller 104 may be attached to the body 106 of the sterilization container 102. In other embodiments, the controller 104 may be attached to the container lid 108. In still other embodiments, the controller 104 may be separate from the sterilization container 102 but in operative communication with the transmission pathway 116, e.g., by either a wired or wireless connection between the controller 104 and the transmission pathway 116. Further, the controller 104 is sterilizable with the container body 106 and container lid 108. That is, the controller 104 is capable of being subjected to a sterilization protocol in which the controller 104 may be exposed to elevated temperatures, elevated pressures, and/or one or more sterilizing agents, such as ethylene oxide, hydrogen peroxide, or ozone. Additionally, the controller 104 may be replaceable, e.g., the controller 104 may be disposed within a housing 124 that is attached to the sterilization container 102 (i.e., the body 106 or lid 108) and the controller 104 may be replaced after a period of use, after a specified number of sterilization cycles, or the like. In some embodiments, the controller 104 may activate an indicator to alert the user that the controller 104 should be replaced. Moreover, the housing 124 may include a vent 126, e.g., to allow adequate cool down and drainage of an interior of the housing 124, where the controller 104 is located, following sterilization of the sterilization container assembly 100.

In other embodiments, other devices for detecting a breach in the sterilization container seal may be used. For instance, in some embodiments, a reed switch may be installed on the sterilization container to detect whether the container is and remains properly sealed. In such embodiments, the reed switch may comprise an actuating magnet fixed on the container lid 108 and a switch fixed on the container body 106 or embedded in the container gasket 112. The magnet and switch may not properly align or may become misaligned, e.g., if the container gasket 112 is damaged or degraded, e.g., if there is an obstruction preventing the lid 108 from properly seating with respect to the body 106, or if the gasket 112 is disturbed, for example by dropping the container 102, after the container 102 is sealed. Thus, if the magnet and switch are not properly aligned to close or to open the circuit into which the switch is integrated (i.e., the switch may be configured to be normally open or normally closed), an indicator may be activated to indicate to a user of the sterilization container 102 that the container 102 is not properly sealed and its contents potentially are subject to contamination.

The present disclosure also provides methods for detecting a breach in sterility of the sterilization container 102. Referring to FIG. 3, an exemplary method 300 comprises sealing the sterilization container 102 using a gasket 112 that extends between a container body 106 and a container lid 108, as shown at 310. The container 102 may be sealed, e.g., by latching the lid 108 with respect to the body 106 to compress the gasket 112 between the lid 108 and body 106, but the container 102 may be sealed in other ways as well.

As described with respect to FIGS. 1, 2A, and 2B, the sterilization container 102 preferably comprises a sterility breach detection system 114, including a transmission pathway in the container gasket 112 and a controller 104 for sending one or more signals along the transmission pathway 116, i.e., the controller 104 is in operative communication with the transmission pathway 116. After the container 102 is sealed, the method 300 comprises sending a first signal along the transmission pathway 116, as shown at 320 in FIG. 3. The first signal may be sent by the controller 104 to establish a baseline signal value. Next, the method 300 includes at 330 sterilizing the sterilization container 102 and its contents according to any appropriate sterilization protocol. Then, as illustrated at 340 and 350, the method 300 comprises sending a detection signal along the transmission pathway 116 and processing the detection signal. Preferably, the detection signal is both sent and processed by the controller 104. In exemplary embodiments, the detection signal is processed using time domain reflectometry (TDR) as described herein.

Method 300 further includes determining whether a breach exists in the gasket 112, as shown at 360, and if so, alerting a user of the sterilization container 102 that a breach exists in the gasket 112, as depicted at 370. For instance, the controller 104 may compare the detection signal to the baseline signal value, which was established by the first signal sent prior to sterilizing the container 102 as previously described, to determine whether a breach exists in the gasket 112. In some embodiments, if the detection signal exceeds a predetermined signal value, the controller 104 activates an indicator to alert the user that a breach exists in the container gasket 112. It will be appreciated that a breach in the gasket 112 includes any abnormality in the seal between the container lid 108 and container body 106, e.g., a loosening of the seal between the lid 108 and body 106 in one or more areas due to damage to or degradation of the gasket 112. Such abnormality could impact the sealing effectiveness and thereby potentially compromise the sterility of the contents of the sterilization container 102. Further, the user may be alerted to the breach using any suitable means, e.g., by the activation of one or more visual and/or audible indicators. As shown at 380 in FIG. 3, if no breach is detected and the container 102 remains closed (and, therefore, remains sealed because no breach in the seal has been detected), the controller 104 may continue to send detection signals to determine if the seal is breached until the container 102 is opened.

Turning now to FIGS. 4 through 12, the present disclosure further provides a controller system 200 that, for example, may detect, track, and alert a user to the state of a sterilization container such as container 102. The controller system 200 and the sterilization container 102 may be part of the sterilization container assembly 100. In exemplary embodiments, the assembly 100 also includes a sterility breach detection system 114 as described herein.

In exemplary embodiments, the controller system 200 is a reusable system that is based on an embedded hardware architecture and includes an array of various sensors and indictors to help detect, track, and alert the user to the state of the sterilization container 102. For example, the controller system 200 may detect and display basic information such as that the container 102 has undergone adequate thermal cycling, i.e., thermal cycling adequate to sterilize the contents of the container 102, or that a breach exists in the container lid 108. However, the controller system 200 also may be capable of performing more advanced functions that would not be possible with traditional indicators. Such advanced functions may include, but are not limited to, detection of excessive mechanical shock, asset tracking, counting thermal cycles, counting lid closures, and content tracking.

Further, as shown in FIG. 4, the controller system 200 may be used in conjunction with the sterility breach detection system 114, which comprises a smart gasket 112 positioned between the container body 106 and container lid 108 that seals an interior 110 of the container 102 against an ingress of contaminants and is configured to detect a breach in the seal between the body 106 and lid 108. It will be appreciated that FIG. 4 illustrates only a portion of the smart gasket 112, which extends around the entire interface between the container body 106 and lid 108 to seal the container 102. As described above, the smart gasket 112 preferably includes a transmission pathway 216 embedded therein for detecting a breach in the container seal using TDR, but in other embodiments, the smart gasket 112 may include the switch portion of a reed switch and the magnet portion of the reed switch may be attached to the container lid 108. In still other embodiments, the smart gasket 112 may comprise a conductivity sensor, e.g., the gasket 112 includes a conductive strip that mates with two conductive pads that may be disposed on the container lid 108 or container body 106. Once the conductive strip mates with the conductive pads, a circuit is closed that is detected by the microcontroller 202 and indicates proper attachment or closure of the gasket 112 with the container body 106 and lid 108 such that the sterilization container 102 is sealed against the ingress of contaminants. Of course, in some embodiments, the controller system 200 may be used in a sterilization container assembly 100 without the sterility breach detection system 114, e.g., the controller system 200 may be used with a standard gasket rather than a smart gasket 112. In such embodiments, the controller system 200 includes a plurality of other sensors and indicators, examples of which are provided herein, to help detect, track, and alert the user to the state of the sterilization container 102. Further, in some embodiments, the sterility breach detection system 114, including smart gasket 112, may be used without the controller system 200, as described herein.

Referring to FIG. 5, a block diagram of the controller system 200 is provided, according to an exemplary embodiment of the present subject matter. Central to the controller system 200 is a micro-controller unit (MCU) or microcontroller 202. The purpose of the microcontroller 202 is to store the core logic of the controller system 200, read and write to memory, and read and control various devices via an input/output (I/O) bus. The microcontroller 202 is disposed within a housing 204. Various subsystems are connected to the microcontroller 202, including non-volatile memory 208, sensors 210, real-time clock (RTC) 212, a battery and power regulation subsystem 214, and communications subsystems or indicators 216. The sensors 210 may include sensors that measure temperature, relative humidity, acceleration, pressure, light, ambient noise, magnetic field, location (e.g., via Global Positioning Satellite (GPS) receiver), force, and one or more sterilization agents. For instance, the controller system 200 may include an analog temperature sensor, a relative humidity sensor, an accelerometer, a magnetometer, an ambient light sensor, a capacitive touch sensing subsystem, a pressure sensor, a force sensor or load cell, a strain sensor, a hydrogen peroxide sensor, an ozone sensor, an ethylene oxide sensor, and/or a GPS receiver. Various sensors and their uses in the sterilization container assembly 100 and controller system 200 are described in greater detail herein. The indicators 216 indicate or communicate a state of the sterilization container 102 to a user of the container 102 as further described herein. Further, in exemplary embodiments including the smart gasket 112, the smart gasket 112 is in operative communication with the microcontroller 202, e.g., via one or more cables 230 and a connector 228 as shown in FIGS. 4 and 8. It will be appreciated that, when the smart gasket 112 is used in conjunction with the controller system 200, the microcontroller 202 of the controller system 200 may be or may take the place of the controller 104, i.e., the microcontroller 202 may perform the functions described above as performed by the controller 104. For instance, where the smart gasket 112 utilizes TDR to detect a breach in the seal between the body 106 and lid 108 of the container 102, the microcontroller 202 is configured to send a signal along the transmission pathway 116, receive a reflected signal, and process the reflected signal. Moreover, as shown in FIG. 7, industry standard printed circuit boards (PCBs) 218 may be used to fix and interconnect the various electronic components. Thus, the microcontroller 202 is in operative communication with the sensors 210, the indicators 216, and other electronic components, e.g., to receive data or inputs from one or more sensors 210, process the data or inputs as needed, and activate one or more indicators 216 based on the data or inputs.

Referring particularly to FIGS. 6 and 7, the electronic components and power sources are housed within the housing 204, which provides structural and thermal protection from the external environment. The housing 204 has an external shell 220 that is constructed from an autoclave compatible material such as stainless steel, aluminum, or high-temperature polymer. An additional layer of thermal insulation 220 may be added inward of the external shell 220 to provide additional buffer between the electronic components and autoclave environment. The indicators 216 are located external to the electronic controller enclosure, i.e., in or on the external shell 220 of housing 204, to indicate or communicate various states of the sterilization container 102 to a user.

The indicators 216 may be made from LED or LCD based technology, or any other suitable indicator type may be used. As shown in FIG. 6, in an exemplary embodiment of the controller system 200, three LED indicators 216 are disposed in the external shell 220 of the housing 204 such that the indicators 216 are retained in the housing 204 yet are visible to a user. In the depicted embodiment, the three indicators 216 are two red LEDs 216a, 216b and one green LED 216c. The two red LEDs include a shock indicator 216a and an insufficient temperature or seal indicator 216b, and the green LED is a sufficient temperature or seal indicator 216c. Where the indicators 216b, 216c indicate a state of the container seal, the seal state may be determined based on a state of the container gasket 112. For example, the sterilization container system 100 may be configured to detect a breach in the gasket 112, which would indicate a breach in the seal between the container body 106 and container lid 108, potentially comprising the sterility of the container interior 110. If no breach is detected in the gasket 112, the green LED indicator 216c may be illuminated (or on) and the red LED indicator 216b remains unilluminated (or off), but if a breach is detected in the gasket 112, the red LED indicator 216b rather than the green indicator 216c may be illuminated. As described in greater detail herein, whether a breach exists in the gasket 112 may be detected using a transmission pathway 116 embedded in the gasket 112 and TDR technology or using a reed switch. Further, some embodiments of the container assembly 100 and controller system 200 may include only one indicator 216 for alerting a user to a breach in the gasket 112, e.g., the microcontroller 202 may be configured to activate the one indicator 216 if the container 102 is not sealed against the ingress of contaminants. Additionally, in some embodiments, the indicators 216 may be labeled directly on the external shell 220 of the housing 204, but in other embodiments, a user manual or other literature may inform the user what is indicated by each indicator 216.

Of course, the controller system 200 also may have additional and/or different indicators 216. The indicators 216 may be positioned on one or more sides 224 of the housing 204. Moreover, one or more other components of the sterilization container assembly 100 or controller system 200 may be positioned on or extend through one or more housing sides 224, such as first side 224a, second side 224b, third side 224c, and fourth side 224d shown in FIGS. 7-9. In the depicted exemplary embodiment, such other components include an on/off or power switch 226 (which may be a toggle switch as shown in FIG. 8 or any other suitable switch), a connector 228 for the smart gasket 112 (which places the transmission pathway 116 and microcontroller 202 in operative communication via one or more cables 230, such that the microcontroller 202 functions as the controller 104 described above), and an analog temperature sensor 210a. As illustrated in FIG. 8, the switch 226 and connector 228 may be on the fourth side 224d of the housing 204, and as shown in FIG. 9, the temperature sensor 210a may be on the third side 224c of the housing 204. Other sensors 210 also may extend through or be positioned on the external shell 220 of the housing 204. On the other hand, some sensors 210, such as the accelerometer 210b shown in FIG. 7, need not be exposed to the external environment and, therefore, may be housed within the housing 204, i.e., in an interior 232 of the housing 204 inward of the external shell 220 and insulation 222. It will be appreciated that the controller system 200 illustrated in FIGS. 4 and 6-9 is by way of example only, and the sensors 210, indicators 216, and other components (such as the switch 226 and connector 228) may be positioned on or extend through any suitable side 224 of the housing 204 or may be positioned within the housing interior 232 (e.g., on a PCB 218) at any suitable location.

As previously described, the sterilization container assembly 100 and controller system 200 may include a plurality of sensors 210. Suitable sensors 210 are available that utilize various technology and packaging configurations. Further, suitable sensors 201 may be adapted for robust industrial and/or automotive use (e.g., with minimal drift or hysteresis following prolonged exposure at limits), such that the sensors 210 are adapted for use in the sterilization environment, which typically involves relatively high temperatures (e.g., +125° C.) and pressures and also may involve exposure to steam and/or one or more sterilizing agents such as ethylene oxide, hydrogen peroxide, and/or ozone. Each sensor 210 of the plurality of sensors 210 may be selected from a group of sensors that consists of a temperature sensor, relative humidity sensor, accelerometer, pressure sensor, light sensor, lid latch engagement sensor, ambient noise sensor, magnetic field sensor, Global Positioning Satellite (GPS) receiver, hydrogen peroxide sensor, ozone sensor, ethylene oxide sensor, and force sensor. Other sensors 210 may be used as well, and in some embodiments, more than one of a single type of the foregoing sensors may be included in the assembly 100. For example, the sterilization container assembly 100 may include a plurality of force sensors 210a, e.g., each force sensor 210c may be a load cell that is positioned on a bottom support 234, such as a foot or a bottom surface, of the container body 106.

Further, it will be appreciated that data or inputs from two or more sensors 210 may be used in conjunction with one another to determine or provide a state of the sterilization container 102. The state of the container 102 may then be indicated to a user by the activation of one or more indicators 216. For instance, referring to FIG. 10, the controller system 200 may include a thermal cycle counter that uses inputs or data from a temperature sensor 210a and a pressure sensor 210d in conjunction with the MCU or microcontroller 202 to count the number of thermal and/or pressure cycles. The number of thermal and pressure cycles may indicate whether the sterilization container 102 has been subjected to sufficient temperature and pressure to sterilize the contents of the container 102, or the thermal cycle count may be used to determine when components of the sterilization container assembly 100, including the sterility breach detection system 114 and controller system 200, should be replaced. A corresponding indicator 216 may be activated to indicate to the user that the container contents are sterile or that a component of the assembly 100 needs to be replaced.

More particularly, FIG. 10 illustrates a thermal cycle counter logic sequence 1000 according to an exemplary embodiment of the present subject matter. As shown at 1010 and 1020 in the logic diagram of FIG. 10, temperature is measured using the temperature sensor 210a and pressure is measured using the pressure sensor 210d. As illustrated at 1030 and 1040, the microcontroller 202 determines whether the measured temperature exceeds a preset temperature threshold and whether the measured pressure exceeds a preset pressure threshold. If both the temperature and pressure exceed their present thresholds, the microcontroller 202 increments a thermal cycle counter, as shown at 1050. However, if either the temperature or the pressure does not exceed its preset threshold, the microcontroller 202 does not increment the thermal cycle counter. Rather, if the temperature does not exceed its preset temperature threshold, the microcontroller 202 continues to monitor the temperature measurements to determine if the temperature does exceed its preset threshold. Similarly, if the pressure does not exceed its preset temperature threshold, the microcontroller 202 continues to monitor the pressure measurements to determine if the pressure does exceed its preset threshold. The controller system 200 also may include a master counter reset, depicted at 1060 in FIG. 10, which may be logic utilizing inputs from certain sensors 210 or a switch that may be manipulated by a user. When triggered, the master counter reset may reset the thermal cycle counter (and also may reset any other counters in the logic of the controller system 200) such that the thermal cycle counter is incremented to one (1) when both the temperature and pressure next exceed their preset thresholds. For example, the master counter reset may be triggered once the thermal cycle counter reaches a preset number of cycles, which may represent a sufficient number of cycles for sterilizing the contents of the container 102. As another example, the master counter reset may be triggered when a user manually manipulates a switch (e.g., on the housing 204, container body 106, or container lid 108), which may indicate that soiled articles have been placed in the interior 110 of the container 102 and the user is initiating a sterilization protocol to sterilize the articles in the container 102. The master counter reset may be triggered in other ways as well. Finally, as shown at 1070 and 1080, the microcontroller 202 determines whether the thermal cycle counter has reached a preset number of cycles and, if so, activates an indicator 216. As previously described, the indicator 216 may indicate to a user of the container assembly 100 that the container contents are sterile or that the container assembly 100 has undergone a number of thermal cycles after which one or more components of the assembly should be replaced.

The controller system 200 also may include a lid closure counter, which may be used in conjunction with the thermal cycle counter to differentiate the number of lid opening cycles from sterilization. An exemplary lid closure counter may utilize an ambient light sensor 210e, which detects changes in the ambient light within the sterilization container 102 to determine if the lid 108 has been opened and closed, or a lid latch engagement sensor 210f (e.g., a mechanical micro switch or a magnetic reed switch), which detects when the lid 108 is engaged with or disengaged from the container body 106.

Further, the content tracking function listed above may be configured similar to self-checkout technology at grocery stores. More particularly, the container body 106 may be equipped with force sensors or load cells 210c on its bottom support 234, e.g., the body 106 may be supported on a plurality of feet and a force sensor or load cell 210c may be disposed on each foot. The sum of the loads measured by the sensors 210c indicates the mass of the sterilization container assembly 100 plus the contents within the interior 110 of the container 102. The mass of the container assembly 100 is known. A representative mass of the articles that are sterilizable within the container 102 may be measured individually and recorded in a database, which can be stored in the non-volatile memory 208 of the controller system 200. Once all the contents of the container 102 is loaded in the container, the mass of the contents, as measured by the sensors 210c, may be compared to predicted total content mass based on the total mass of the types of instruments or articles typically used for a particular procedure, which is computed using the mass of each instrument or article for the particular procedure that is stored in the database. The comparison may be performed local to the MCU or microcontroller 202. Thus, if the mass of the container contents is less than the predicted total content mass for the procedure, the microcontroller 202 may activate an indicator 216 to indicate to a user of the sterilization container assembly 100 that one or more instruments or articles requiring sterilization after the procedure may not be within the sterilization container 102. It will be appreciated that a margin of error, such as 5%, 10%, or 15%, may be applied to the predicted total mass such that the measured mass need not be exactly equal to the predicted mass to avoid triggering the indicator 216. Rather, as an example, if the measured mass was more than 10% less (or more than 10% greater) than the predicted mass, the microcontroller 202 would activate the indicator 216, but if the measured mass was within 10% of the predicted mass, the indicator 216 would not be activated.

Moreover, a relative humidity sensor 210g can be used to measure the relative humidity of the container interior 110 post sterilization, e.g., to ensure that adequate cooling and drainage has occurred. In some embodiments, the relative humidity data from sensor(s) 210g is used in conjunction with the temperature sensor 210a to shorten the cool down period after sterilization. As such, the data from the temperature and relative humidity sensors 210a, 210g could be used to hasten turnaround of the container 102 through the sterilization protocol.

Further, an ambient noise sensor 210h may be useful, provided its data or inputs are associated with or subjected to appropriate filtering and detection logic. For example, the ambient noise sensor 210h may be used to detect the typical sound of a closure of the container lid 108, a closure of an autoclave door, and/or a transfer of the container 102, which sounds may be used to track the status of the sterilization container 102 and/or alert a user to the status of the container 102, e.g., whether the container 102 has been sterilized, whether the lid 108 has been disturbed after sterilization, whether the lid 108 has been disturbed since the contents were loaded into the container 102, etc. As another example, the noise level detected by the ambient noise sensor 210h may be used to determine if the container 102 has been dropped or hit upon, which could affect the seal between the container body 106 and lid 108 (thereby potentially compromising the sterility of the container contents) or could damage the container 102 (potentially compromising its ability to maintain sterility) or its contents (potentially compromising the effectiveness or usefulness of the articles or instruments).

Additionally or alternatively, the sterilization container assembly 100 may include a magnetic field sensor 210i. The magnetic field sensor 210i may be used in conjunction with the accelerometer 210b to track the position of the assembly 100 and the contents of the container 102 within a hospital building. For instance, the magnetic field sensor 210i may be used as part of an asset tracking system. In other embodiments, a GPS receiver 210j may be used as part of an asset tracking system, e.g., to track the container 102 and its contents when a hospital building. Still further, the sterilization container assembly 100 may comprise a sterilization agent sensor 210k for detecting a sterilization agent used during the sterilization process. More specifically, the assembly 100 may include a sensor 210k that is one of a hydrogen peroxide sensor, an ozone sensor, an ethylene oxide sensor, or a sensor configured to detect any other agent that may be used in the sterilization of the sterilization container 102. The sterilization agent sensor 210k may be affixed to or within the container body 106, the container lid 108, or the housing 204 and may be in operative communication with the microcontroller 202. When the microcontroller 202 detects a preset threshold amount of the particular sterilizing agent (e.g., hydrogen peroxide, ozone, ethylene oxide, or the like), the microcontroller 202 may determine that the sterilization container assembly 100, specifically the sterilization container 102, has been subjected to sufficient sterilizing agent to render the contents of the container 102 sterile. As a result, the microcontroller 202 may activate an indicator 216 to signal to a user that the contents of the container 102 are sterile.

Referring to FIGS. 6, 11, and 12, additional logic that may be programmed in the microcontroller 202 will be described. As shown in FIG. 6, the controller system 200 may include three LED indicators 216 in one side 224 (e.g., first side 224a as shown) of the housing 204, e.g., two red LEDs and one green LED arranged in a row, with one red LED on the left, one red LED in the center, and the green LED on the right. As previously described, the red LED on the left may be a shock indicator 216a, the red LED in the center may be an insufficient temperature or seal indicator 216b, and the green LED on the right may be a sufficient temperature or seal indicator 216c.

Referring particularly to FIG. 11, an exemplary logic sequence 1100 for activating indicator 216a is provided. As illustrated at 1110, the microcontroller 202 determines whether the sterilization container assembly 100 has been subjected to an acceleration magnitude greater than 5 g. If so, the left red LED indicator 216a is activated to be solidly lit, as shown at 1120, thereby alerting a user of the sterilization container assembly 100 that the assembly has experienced a shock, e.g., has been dropped, hit, or otherwise experienced an impact. If the acceleration magnitude does not exceed 5 g, the indicator 216a remains off or unlit as shown at 1130, which indicates to the user that the sterilization container assembly 100 has not experienced a shock. It will be appreciated that the acceleration of the assembly 100 may be measured be an accelerometer, such as the accelerometer 210b described herein that may be within the controller housing 204 or may be on or within the sterilization container 102.

Turning to FIG. 12, an exemplary logic sequence 1200 for activating indicators 216b and 216c is provided. As shown at 1210, the microcontroller 202 determines whether sufficient gasket pressure is applied, e.g., using TDR technology as described above with respect to one embodiment of smart gasket 112. If an insufficient gasket pressure is applied, as shown at 1220, the microcontroller 202 activates the middle or center red LED indicator 216b, e.g., in a flashing or blinking pattern, to alert a user of the sterilization container 102 that the container is not properly sealed to maintain the sterility of the container's contents post-sterilization. However, if the microcontroller 202 determines that a sufficient gasket pressure is being applied, the microcontroller 202 next determines whether a temperature threshold has been achieved, as shown at 1230. If not, as illustrated at 1240, the microcontroller 202 activates the center red LED indicator 216b, e.g., such that the indicator 216b remains solidly activated without blinking or flashing, to alert the user that the contents of the sterilization container 102 have not achieved a sufficient temperature for sterilization. If the temperature threshold has been achieved, the center red LED indicator 216b remains off or is not activated, as shown at 1250, and the right green LED indicator 216c is activated as depicted at 1260, such that the indicator 216c remains solidly activated (i.e., without blinking or flashing). The solid green LED indicator 216c thereby indicates to the user that the contents of the sterilization container 102 have been sterilized and remain sterilized.

Accordingly, the present subject matter provides sterilization container assemblies having one or more advantages. For example, a sterilization container assembly may comprise a sterility breach detection system, which may utilize a smart gasket disposed between a body and a lid of a sterilization container to detect breaches in the gasket and, thus, in the seal between the container body and lid. In exemplary embodiments, the sterility breach detection system utilizes time domain reflectometry to assess the gasket quality, e.g., by sending signals along a transmission pathway embedded in the gasket. As another example, a sterilization container assembly may comprise a controller system for detecting, tracking, and alerting a user to one or more states of a sterilization container of the assembly. The controller system may include a plurality of sensors and a plurality of indicators, where the sensors are used to detect and track the container's state, which is communicated to the user via the indicators. In exemplary embodiments, the sterilization container assembly includes both the sterility breach detection system and controller system, such that the controller system at a minimum detects, tracks, and alerts a user to whether the interior of the sterilization container, and thus its contents, are sterile. Other advantages of the present subject matter also may be apparent to one of ordinary skill in the art.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sterilization container system, comprising:
   a sterilization container including
   a container body,
   a container lid, the container body and container lid together defining a container interior,
   a container gasket for sealing the container interior against an ingress of contaminants, and
   a transmission pathway embedded in the container gasket; and
   a controller,
   wherein the controller is configured to process a signal transmitted along the transmission pathway to determine whether a breach exists in the container gasket, and
   wherein the transmission pathway is a metal wire.

2. The sterilization container system of claim 1, further comprising a ground wire coaxial with the transmission pathway.

3. The sterilization container system of claim 2, wherein the container body and the container lid are each formed from a metallic material such that the container body is metallic and the container lid is metallic.

4. The sterilization container system of claim 3, wherein the container gasket is a dielectric material disposed between the metal wire transmission pathway, the metallic container body, and the metallic container lid.

5. The sterilization container system of claim 1, wherein the controller is configured to send and receive the signal.

6. The sterilization container system of claim 1, wherein the controller is configured to process the signal using time domain reflectometry.

7. The sterilization container system of claim 1, wherein the container gasket defines a sealing pathway, and wherein the transmission pathway is coextensive with the sealing pathway.

8. The sterilization container system of claim 1, wherein the controller is sterilizable with the container body and container lid.

9. The sterilization container system of claim 1, wherein the controller is attached to the container body.

10. The sterilization container system of claim 1, wherein the transmission pathway includes local variances in impedance.

11. The sterilization container system of claim 1, wherein the controller is configured to establish a baseline signal value before the sterilization container undergoes a sterilization protocol.

12. The sterilization container system of claim 11, wherein the controller is configured to send a detection signal along the transmission pathway after the sterilization container undergoes the sterilization protocol.

13. The sterilization container system of claim 12, wherein the controller is configured to compare the detection signal to the baseline signal value to determine whether a breach exists in the gasket.

14. The sterilization container system of claim 12, further comprising:
   an indicator for indicating a state of the sterilization container to a user of the sterilization container.

15. The sterilization container system of claim 14, wherein the controller is configured to activate the indicator if the detection signal exceeds a predetermined signal value.

16. A sterilization container system, comprising:
   a sterilization container including a container body and a container lid, the container body and container lid together defining a container interior, the sterilization container further including a container gasket for sealing the container interior against an ingress of contaminants and a transmission pathway embedded in the container gasket;
   a sensor attached to the sterilization container;
   an indicator disposed on the sterilization container for indicating a state of the sterilization container to a user of the sterilization container; and
   a controller in operative communication with the sensor, wherein the transmission pathway is a metal wire, and wherein the controller is configured to process data from the sensor to activate the indicator.

17. The sterilization container system of claim 16,
wherein the controller is configured to send a signal along the transmission pathway, receive a reflected signal, and process the reflected signal, and
wherein the controller is configured to activate the indicator if the reflected signal indicates the sterilization container is not sealed against the ingress of contaminants.

18. The sterilization container system of claim 16, further comprising:
a plurality of sensors in operative communication with the controller.

19. The sterilization container system of claim 18, wherein each sensor of the plurality of sensors is selected from the group consisting of temperature sensor, relative humidity sensor, accelerometer, pressure sensor, light sensor, ambient noise sensor, magnetic field sensor, Global Positioning Satellite (GPS) receiver, hydrogen peroxide sensor, ozone sensor, ethylene oxide sensor, and force sensor.

20. A sterilization container system, comprising:
a sterilization container including
a container body,
a container lid, the container body and container lid together defining a container interior,
a container gasket for sealing the container interior against an ingress of contaminants, and
a transmission pathway embedded in the container gasket;
a plurality of sensors;
an indicator for indicating a state of the sterilization container to a user of the sterilization container; and
a controller in operative communication with the transmission pathway and the plurality of sensors,
wherein the transmission pathway is a metal wire,
wherein the controller is configured to process a signal transmitted along the transmission pathway to determine whether a breach exists in the container gasket, and
wherein the controller is configured to activate the indicator to indicate to a user that a breach exists in the container gasket.

* * * * *